(12) United States Patent
Chen et al.

(10) Patent No.: US 11,229,553 B2
(45) Date of Patent: Jan. 25, 2022

(54) DRESSING APPARATUS AND METHODS FOR FACILITATING HEALING

(71) Applicant: SYNAPTIVE MEDICAL INC., Toronto (CA)

(72) Inventors: Sean Jy-Shyang Chen, Toronto (CA); Alison-Jean Kramer, Toronto (CA); Gal Sela, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 1099 days.

(21) Appl. No.: 15/238,128

(22) Filed: Aug. 16, 2016

(65) Prior Publication Data

US 2018/0049923 A1 Feb. 22, 2018

(51) Int. Cl.
*A61F 13/00* (2006.01)

(52) U.S. Cl.
CPC .. *A61F 13/00055* (2013.01); *A61F 13/00042* (2013.01); *A61F 13/00051* (2013.01); *A61F 13/00987* (2013.01); *A61F 2013/00429* (2013.01)

(58) Field of Classification Search
CPC .......... A61F 13/00042; A61F 13/00055; A61F 13/00987; A61F 13/00051; A61F 2013/00944; A61F 2013/00957; A61F 2013/00961; A61F 2013/00953; A61F 2013/0097; A61F 2013/00927

See application file for complete search history.

(56) References Cited

U.S. PATENT DOCUMENTS

| 8,514,067 | B2 | 8/2013 | Hyde et al. |
| 8,599,009 | B2 | 12/2013 | Hyde et al. |
| 8,723,640 | B2 | 5/2014 | Hyde et al. |
| 8,774,885 | B2 | 7/2014 | Abreu |
| 8,816,814 | B2 | 8/2014 | Hyde et al. |
| 8,914,089 | B2 | 12/2014 | Abreu |
| 2003/0069489 | A1 | 4/2003 | Abreu |
| 2010/0160794 | A1* | 6/2010 | Banet ................... A61B 5/0022 600/485 |
| 2013/0046477 | A1 | 2/2013 | Hyde et al. |
| 2013/0172691 | A1 | 7/2013 | Tran |
| 2013/0274630 | A1* | 10/2013 | Duesterhoft ......... A61B 5/1477 600/573 |
| 2014/0005618 | A1 | 1/2014 | Locke et al. |

(Continued)

OTHER PUBLICATIONS

Habib, H. (2016). On Body Performance Evaluation of Passive RFID Antennas Inside Bandage (Master's thesis, Tampere University of Technology, Tampere, Finland).

(Continued)

*Primary Examiner* — Camtu T Nguyen

(57) ABSTRACT

A dressing apparatus and methods for facilitating healing, the apparatus and methods involving a dressing member, an electromagnetically conductive element mechanically coupled with the dressing member, and a primary RFID device configured to transmit at least one output signal to the electromagnetically conductive element, to receive at least one return signal from the electromagnetically conductive element, and to provide an alert if the at least one return signal has a strength corresponding to at least approximately a threshold amount of fluid present in the dressing member, whereby healing is facilitated.

17 Claims, 3 Drawing Sheets

(56) References Cited

U.S. PATENT DOCUMENTS

| | | | |
|---|---|---|---|
| 2014/0143064 A1 | 5/2014 | Tran | |
| 2014/0291409 A1* | 10/2014 | Nitta | G06K 19/07758 |
| | | | 235/492 |
| 2015/0065837 A1 | 3/2015 | Abreu | |
| 2015/0085249 A1 | 3/2015 | Abreu | |
| 2015/0087935 A1 | 3/2015 | Davis et al. | |
| 2015/0119666 A1 | 4/2015 | Brister et al. | |
| 2015/0369798 A1* | 12/2015 | Yu | B01L 3/502761 |
| | | | 435/5 |
| 2016/0051735 A1 | 2/2016 | Slepian | |

OTHER PUBLICATIONS

Bacheldor, B. Georgia Tech Researchers Create an RFID-Sensor Medical Patch. RFID Journal.

Mehmood N. et al. A flexible and low power telemetric sensing and monitoring system for chronic wound diagnostics. BioMedical Engineering Online.

\* cited by examiner

DRESSING APPARATUS AND METHODS FOR FACILITATING HEALING

TECHNICAL FIELD

The subject matter of the present disclosure generally relates to medical dressings. More particularly, the subject matter of the present disclosure technically relates to medical dressings, such as bandages and compression bandages. Even more particularly, the subject matter of the present disclosure technically relates to medical dressings, such as bandages and compression bandages, requiring frequent monitoring and changing.

BACKGROUND

In the related art, bandages or dressings need routine changing during a post-surgery period, or a post-trauma period, for speedy healing and for reducing medical complications. Bandages typically need changing every few hours, or few days, depending on the condition of a wound. Current tracking of bandage changes in the related art is manual and depends on the physical examination thereof by nursing staff. This related art technique is imprecise and time consuming. Related art monitoring the condition of a wound, only occurring during a bandage change, is typically merely qualitative; and infections may not be noticed by the nursing staff until well into progression, thereby leading to further injury of the subject as well as possible medical malpractice.

In the related art, some monitoring devices include RFID tags and sensors have been applying them on a bandage for sensing humidity, for monitoring vital signs and temperature by way of a flexible bandage having a conductive ink, and for sensing pressure, via a strain gauge, temperature, and humidity, by way of a wound pad. Also in the related art, a wireless diagnostic tool, having a semiconductor chip disposed under a bandage, has been used for monitoring changes in bandage pressure, moisture level, and local temperature at the wound site.

Accordingly, challenges experienced in the related art include a limited use of RFID tags with humidity sensing technology, humidity sensing techniques that use capacitive effects or resistive effects, sensing techniques for less useful characteristics, sensing techniques for detailed pressure information with only scant sensing of moisture information, sensing techniques for testing parameters of pressure, moisture, and temperature, of a surrounding atmosphere. These related art techniques are not suitable for specific robust use in relation to wound care.

BRIEF SUMMARY

The present disclosure addresses at least many of the foregoing challenges experienced by related art wound care techniques, by way of a dressing apparatus, such as medical dressing, e.g., at least one of a bandage and a compression bandage, comprising radio-frequency identification (RFID) tags for both providing a change-alert and reporting specific wound conditions. The dressing apparatus involves signal reception, signal transmission, and signal processing features, for use in a variety of medical environments, such as critical care units, post-operative units, hospital wards, outpatient environments, first-response field operation environments, first-response ambulatory operation environments, battlefields, mobile army surgical hospitals (MASH), remote marine environments, natural disaster areas, and other mass injury environments, whereby healing of a subject, such as a patient, is facilitated. The dressing apparatus of the present disclosure involves an electrically conductive element configured to fully sense a plurality of parameters, such as detailed pressure information, detailed moisture information, and detailed temperature information by way of conductive thread sensing.

In accordance with an embodiment of the present disclosure, a dressing apparatus for facilitating healing comprises: a dressing member; an electromagnetically conductive element mechanically coupled with the dressing member; and a primary RFID device configured to transmit at least one output signal to the electromagnetically conductive element, to receive at least one return signal from the electromagnetically conductive element, and to provide an alert if the at least one return signal has a strength corresponding to at least approximately a threshold amount of fluid present in the dressing member, whereby healing is facilitated.

In accordance with an embodiment of the present disclosure, a method of fabricating a dressing apparatus for facilitating healing, comprises: providing a dressing member; providing an electromagnetically conductive element mechanically coupled with the dressing member; and providing a primary RFID device, providing the primary RFID device comprising configuring the primary RFID device to transmit at least one output signal to the electromagnetically conductive element, to receive at least one return signal from the electromagnetically conductive element, and to provide an alert if the at least one return signal has a strength corresponding to at least approximately a threshold amount of fluid present in the dressing member, whereby healing is facilitated.

In accordance with an embodiment of the present disclosure, a method of facilitating healing by way of a dressing apparatus, comprises: providing a dressing apparatus, providing the dressing apparatus comprising: providing a dressing member; providing an electromagnetically conductive element mechanically coupled with the dressing member; and providing a primary RFID device, providing the primary RFID device comprising configuring the primary RFID device to transmit at least one output signal to the electromagnetically conductive element, to receive at least one return signal from the electromagnetically conductive element, and to provide an alert if the at least one return signal has a strength corresponding to at least approximately a threshold amount of fluid present in the dressing member, whereby healing is facilitated; and applying the dressing apparatus to a wound.

Some of the features in the present disclosure are broadly outlined in order that the section entitled Detailed Description is better understood and that the present contribution to the art by the present disclosure may be better appreciated. Additional features of the present disclosure are described hereinafter. In this respect, understood is that the present disclosure is not limited in its application to the details of the components or steps set forth herein or as illustrated in the several figures of the drawing, but are capable of being carried out in various ways which are also encompassed by the present disclosure. Also, understood is that the phraseology and terminology employed herein are for illustrative purposes in the description and should not be regarded as limiting.

BRIEF DESCRIPTION OF THE DRAWING

The above, and other, aspects, features, and advantages of several embodiments of the present disclosure will be more apparent from the following Detailed Description as presented in conjunction with the following several figures of the Drawing.

Figure 1A:
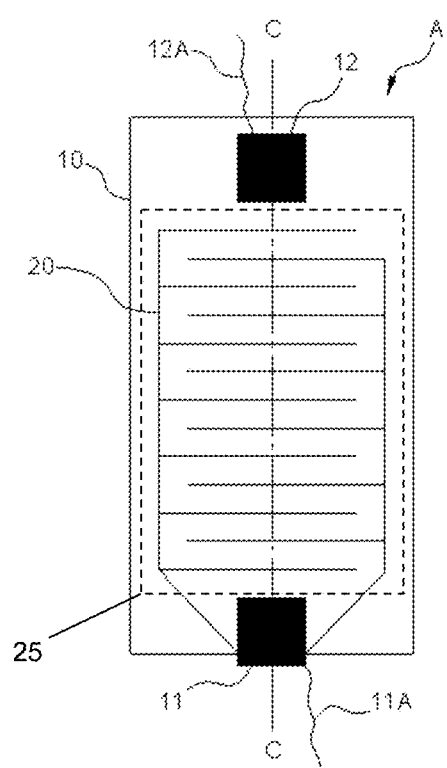
FIG. 1A is a diagram illustrating a top view of a dressing apparatus, in accordance with an embodiment of the present disclosure.

Corresponding reference numerals or characters indicate corresponding components throughout the several figures of the Drawing. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiment are often not depicted in order to facilitate a less obstructed view of these various embodiments of the present disclosure.

DETAILED DESCRIPTION

Referring to FIG. 1A, this diagram illustrates, in a top view, a dressing apparatus A for facilitating healing, comprising: a dressing member 10; an electromagnetically conductive element 20 mechanically coupled with the dressing member 10; and a primary RFID device 11 configured to transmit at least one output signal to the electromagnetically conductive element 20, to receive at least one return signal from the electromagnetically conductive element 20, and to provide an alert if the at least one return signal has a strength corresponding to at least approximately a threshold amount of fluid F present in the dressing member 10, e.g., within an effective area 25, whereby healing is facilitated, in accordance with an embodiment of the present disclosure. The primary RFID device 11 couples a primary severed antenna 11A with the electromagnetically conductive element 20 and is configured to sense changes in dampness of the dressing member 10, such as at least one of a bandage and a compression bandage. The apparatus A is adapted to sense a higher ionic content of wound, e.g., higher than that of water alone.

Figure 1B:
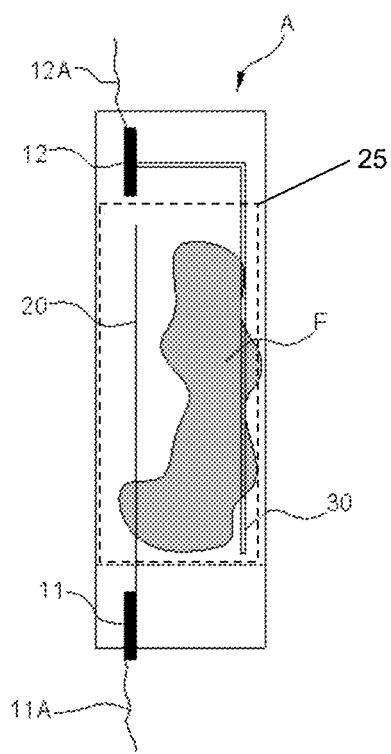
FIG. 1B is a diagram illustrating a cross-sectional side view of a dressing apparatus, in accordance with an embodiment of the present disclosure.

Referring to FIG. 1B, this diagram illustrates, in a cross-sectional side view, taken along a section C-C, a dressing apparatus A for facilitating healing, comprising: a dressing member 10; an electromagnetically conductive element 20 mechanically coupled with the dressing member 10; and a primary RFID device 11 configured to transmit at least one output signal to the electromagnetically conductive element 20, to receive at least one return signal from the electromagnetically conductive element 20, and to provide an alert if the at least one return signal has a strength corresponding to at least approximately a threshold amount of fluid F present in the dressing member 10, e.g., within an effective area 25, whereby healing is facilitated, in accordance with an embodiment of the present disclosure.

Referring back to FIGS. 1A and 1B, the primary RFID device 11 is further configured to measure and transmit information relating to at least one parameter of a dressing application time, a calibration, and any other relevant parameter. The apparatus A further comprises a secondary RFID device 12, coupling a secondary severed antenna 12A with at least one temperature sensor 30, configured to communicate with the primary RFID device 11 and to receive and transmit the information relating to at least one parameter of a dressing application time, a calibration, and any other relevant parameter.

Still referring back to FIGS. 1A and 1B, the primary RFID device 11 comprises a passive read-only RFID tag configured to electromagnetically communicate with the electromagnetically conductive element. The secondary RFID device 12 comprises a passive read-write RFID tag configured to electromagnetically communicate with at least the passive read-only RFID tag. At least one of the primary RFID device 11 and the secondary RFID device 12 are sterilizable. The electromagnetically conductive element 20 comprises at least one of an electromagnetically conductive thread and an extended antenna. The electromagnetically conductive element 20 is at least one of embeddable, interlaceable, and interweavable in relation to the dressing member 10. The dressing member 10 comprises at least one of a bandage and a compression bandage, the fluid F comprises a wound discharge, and the strength of the at least one return signal is variable in relation to an ionic content of the wound discharge. The primary RFID device 11 and the secondary RFID device 12, together, cooperate in a passive operation mode, e.g., in relation to the fluid F.

Still referring back to FIGS. 1A and 1B, the apparatus A further comprises at least one temperature sensor 30 for monitoring a wound temperature, the primary RFID device 11, the secondary RFID device 12, and the at least one temperature sensor 30, together, cooperate in an active operation mode, whereby a wound healing progress is indicatable, and whereby a possible infection is detectable. The at least one temperature sensor 30 comprises at least one of a micro-thermocouple having an ending portion and a micro-thermistor. The at least one temperature sensor 30 is at least one of disposable, biocompatible, and sterilizable. It is to be understood that the apparatus A is not intended to be limited to the components as shown in FIGS. 1A and 1B. Some embodiments of Apparatus A may further comprise one or more of: a pressure sensor to determine if the wound area is overloaded, preventing further injury and/or formation of pressure sores; a detection device to signal an alarm if the bandage has entered or left a predetermined area; a detector to signal an alarm when a RFID device is tampered with or destroyed, including detection if the bandage was removed or loosened; and/or activation and/or deactivation methods for the RFID device to register with the monitoring system.

Figure 2:
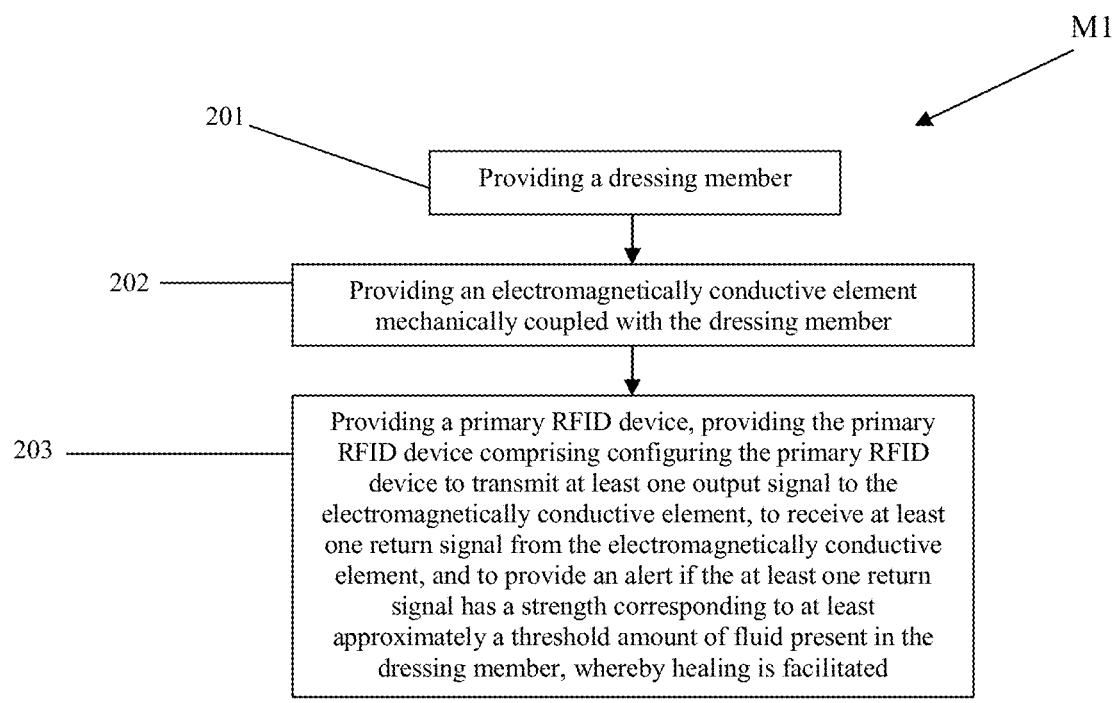
FIG. 2 is a flow diagram illustrating a method of fabricating a dressing apparatus, in accordance with an embodiment of the present disclosure.

Referring to FIG. 2, this flow diagram illustrates a method M1 of fabricating a dressing apparatus A, in accordance with an embodiment of the present disclosure. The method M1 comprises: providing a dressing member 10, as indicated by block 201; providing an electromagnetically conductive element 20 mechanically coupled with the dressing member 10, as indicated by block 202; and providing a primary RFID device 11, providing the primary RFID device 11 comprising configuring the primary RFID device 11 to transmit at least one output signal to the electromagnetically conductive element 20, to receive at least one return signal from the electromagnetically conductive element 20, and to provide an alert if the at least one return signal has a strength corresponding to at least approximately a threshold amount of fluid F present in the dressing member 10, whereby healing is facilitated, as indicated by block 203.

Still referring to FIG. 2, in the method M1, providing the primary RFID device 11, as indicated by block 203, comprises further configuring the primary RFID device 11 to measure and transmit information relating to at least one parameter of a dressing application time, a calibration, and any other relevant parameter. The method M1 further comprises providing a secondary RFID device 12, providing the secondary RFID device 12 comprising configuring the secondary RFID device 12 to communicate with the primary RFID device 11 and to receive and transmit the information relating to at least one parameter of a dressing application time, a calibration, and any other relevant parameter, as indicated by block 204.

Still referring to FIG. 2, in the method M1, providing the primary RFID device 11, as indicated by block 203, comprises providing a passive read-only RFID tag, providing the passive read-only RFID tag comprises configuring the passive read-only RFID tag to electromagnetically communicate with the electromagnetically conductive element 20. Providing the secondary RFID device 12, as indicated by block 204, comprises providing a passive read-write RFID tag, providing the passive read-write RFID tag comprises configuring the passive read-write RFID tag to electromagnetically communicate with at least the passive read-only RFID tag, and at least one of providing the primary RFID device 11 and providing the secondary RFID device 12 comprises at least one of providing the primary RFID device 11 and providing the secondary RFID device 12 as sterilizable.

Still referring to FIG. 2, in the method M1, providing the electromagnetically conductive element, as indicated by block 202, comprises providing at least one of an electromagnetically conductive thread and an extended antenna. Providing the electromagnetically conductive element 20 comprises at least one of embedding, interlacing, and interweaving the electromagnetically conductive element 20 in relation to the dressing member 10. Providing the dressing member 10 comprises providing at least one of a bandage and a compression bandage. The fluid F comprises a wound discharge. Configuring the primary RFID device 11 to receive the at least one return signal from the electromagnetically conductive element 20 that is variable in relation to an ionic content of the wound discharge. Providing the primary RFID device 11 and providing the secondary RFID device 12 respectively comprise providing configuring the primary RFID device 11 and configuring the secondary RFID device 12, together, to cooperate in a passive operation mode.

Still referring to FIG. 2, the method Ml further comprises providing at least one temperature sensor 30 for monitoring a wound temperature, as indicated by block 205, wherein providing the primary RFID device 11, providing the secondary RFID device 12, and providing the at least one temperature sensor 30, comprise providing the primary RFID device 11, providing the secondary RFID device 12, and providing the at least one temperature sensor 30, together, to cooperate in an active operation mode, whereby a wound healing progress is indicatable, and whereby a possible infection is detectable. Providing the at least one temperature sensor 30 comprises providing at least one of a micro-thermocouple having an ending portion and a microthermistor. Providing the at least one temperature sensor 30 comprises providing the at least one temperature sensor 30 as at least one of disposable, biocompatible, and sterilizable.

Figure 3:
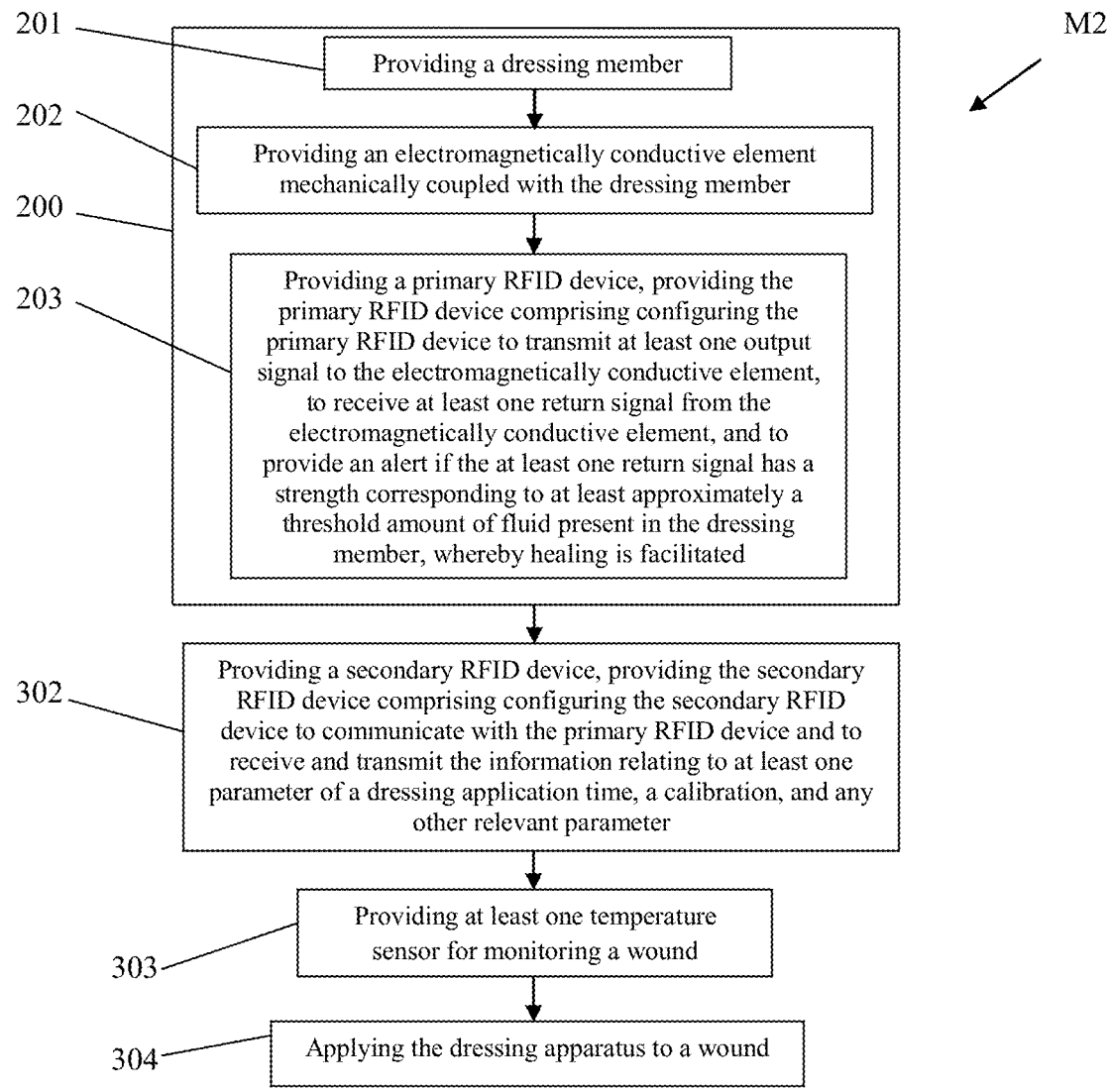
FIG. 3 is a flow diagram illustrating a method of facilitating healing by way of a dressing apparatus, in accordance with an embodiment of the present disclosure.

Referring to FIG. 3, this flow diagram illustrates a method M2 of facilitating healing by way of a dressing apparatus A, in accordance with an embodiment of the present disclosure.

The method M2 comprises: providing the dressing apparatus A, as indicated by block 200, providing a dressing member 10, as indicated by block 301; providing an electromagnetically conductive element 20 mechanically coupled with the dressing member 10, as indicated by block 202; and providing a primary RFID device 11, providing the primary RFID device 11 comprising configuring the primary RFID device 11 to transmit at least one output signal to the electromagnetically conductive element 20, to receive at least one return signal from the electromagnetically conductive element 20, and to provide an alert if the at least one return signal has a strength corresponding to at least approximately a threshold amount of fluid F present in the dressing member 10, whereby healing is facilitated, as indicated by block 203; and applying the dressing apparatus to a wound, as indicated by block 304.

Still referring to FIG. 3, the method M2 further comprises: providing a secondary RFID device 12, providing the secondary RFID device 12 comprising configuring the secondary RFID device 12 to communicate with the primary RFID device 11 and to receive and transmit the information relating to at least one parameter of a dressing application time, a calibration, and any other relevant parameter, as indicated by block 302; and providing at least one temperature sensor 30 for monitoring a wound temperature, wherein providing the primary RFID device 11, providing the secondary RFID device 12, and providing the at least one temperature sensor 30, together, comprise providing the primary RFID device 11, providing the secondary RFID device 12, and providing the at least one temperature sensor 30, to cooperate in an active operation mode, whereby a wound healing progress is indicatable, and whereby a possible infection is detectable, as indicated by block 303.

The dressing apparatus A, e.g., a dressing apparatus having a "severed antenna," is interlaceable into a bandage, for at least that concern, by a user, regarding bandage application consistency is eliminated. In terms of approximate cost of the components for the apparatus A, such costs are minimized, e.g., as follows: (A) RFID components, such as a passive read-only component has a cost range of approximately US$0.01 to approximately US$0.10 per unit, a passive read-write component has a cost range of approximately US $0.05 to approximately US$1.00 per unit, and sterilizable RFID components have a cost range of approximately US$1 to approximately US$2 per unit, wherein examples of sterilizable components which may be used in the apparatus A comprise at least those disclosed via the links, http://www.vizinexrfid.com/gamma-radiation-resistant-asset-tag/ and http://www.verigenics.com/gammatag-rfid-tags.htm), which are hereby incorporated by reference, (B) micro-thermocouple/thermister components, such as disposable biocompatible components which have a cost range of approximately US$0.01 to approximately US$1.00 per unit and sterilizable temperature sensors, wherein examples of sterilizable temperature sensors which may be used in the apparatus A comprise at least those disclosed via the link, (http://www.meas-spec.com/product/temperature/4400Series.aspx) which is hereby incorporated by reference; (C) conductive thread, such as a spool of conductive thread which may have a cost range of approximately US$2 to approximately US$40 wherein examples of conductive thread spools which may be used in the apparatus A comprise at least those disclosed via the link, https://www.sparkfun.com/products/11791 which is hereby incorporated by reference.

Alternatively, an apparatus similar that shown in FIGS. 1A and 1B, using an RFID tag with a severed antenna sensing changes in dampness of a bandage, wherein pure water is used as a test case, demonstrates that the RFID circuit is capable of determining the presence or absence of water. Consequently, the apparatus A is configured to sense a higher ionic content of wound exudates and is even more conductive in relation to wound exudates than in the water test case, whereby the apparatus A is even more sensitive in practical use.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

INDUSTRIAL APPLICABILITY

The subject matter of the present disclosure generally industrially applies to medical dressings. More particularly, the subject matter of the present disclosure industrially applies to medical dressings, such as bandages. Even more particularly, the subject matter of the present disclosure industrially applies to medical dressings, such as bandages, requiring frequent monitoring and changing.

What is claimed:

1. A dressing apparatus for facilitating healing, comprising:
    a dressing member having an effective area;
    an electromagnetically conductive element mechanically coupled with the dressing member, the electrically conductive element comprising a conductive thread and an extended antenna, the extended antenna embedded in the dressing member, and the electrically conductive element, via the conductive thread, configured to sense a plurality of parameters comprising pressure information and moisture information in the effective area; and
    a primary RFID device coupling a primary severed antenna with the electromagnetically conductive element, the primary RFID device configured to transmit at least one output signal to the electromagnetically conductive element, to receive at least one return signal from the electromagnetically conductive element, and to provide an alert, via the primary severed antenna, if the at least one return signal has a strength corresponding to at least approximately a threshold amount of fluid present in the dressing member, the primary RFID device configured to receive at least one return signal from the electromagnetically conductive element that is variable in relation to an ionic content of a wound discharge relative to an ionic content of water alone, the primary RFID device configured to sense changes in dampness of the dressing member in the effective area via the electromagnetically conductive element, and the primary RFID device configured to measure and transmit information, via the primary severed antenna, relating to the plurality of parameters comprising the pressure information and the moisture information in the effective area,
    wherein the fluid comprises the wound discharge,
    wherein the strength of the at least one return signal is variable in relation to the ionic content of the wound discharge relative to the ionic content of the water alone, and
    wherein the electromagnetically conductive element is embedded, interlaced, and interwoven in relation to the dressing member.

2. The apparatus of claim 1, wherein the primary RFID device is further configured to measure and transmit, via the primary severed antenna, information relating to at least one parameter of a dressing application time, a calibration, and-any other relevant parameter.

3. The apparatus of claim 2, further comprising a secondary RFID device coupling a secondary severed antenna with at least one temperature sensor, the secondary RFID device configured communicate, via the secondary severed antenna, with the primary RFID device and to receive and transmit, via the secondary severed antenna, the information relating to information in the effective area.

4. The apparatus of claim 3,
    wherein the primary RFID device comprises a passive read-only RFID tag configured to electromagnetically communicate with the electromagnetically conductive element,
    wherein the secondary RFID device comprises a passive read-write RFID tag configured to electromagnetically communicate with at least the passive read-only RFID tag,
    wherein at least one of the primary RFID device and the secondary RFID device is sterilizable by gamma radiation and clean-in-place (CIP) sterilization, and
    wherein at least one of the primary RFID device and the secondary RFID device is compliant with a Restriction of Hazardous Substances (RoHS) Directive.

5. The apparatus of claim 3, wherein the primary RFID device and the secondary RFID device, together, cooperate in a passive operation mode.

6. The apparatus of claim 3, further comprising at least one temperature sensor for monitoring a wound temperature, the primary RFID device, the secondary RFID device, and the at least one temperature sensor, together, cooperate in an active operation mode.

7. The apparatus of claim 6, wherein the at least one temperature sensor comprises at least one of a micro-thermocouple having an ending portion and a micro-thermistor.

8. The apparatus of claim 6, wherein the at least one temperature sensor comprises is at least one of disposable, biocompatible, and sterilizable.

9. The apparatus of claim 1, wherein the dressing member comprises at least one of a bandage and a compression bandage.

10. A method of fabricating a dressing apparatus for facilitating healing, comprising:
providing a dressing member having an effective area;
providing an electromagnetically conductive element mechanically coupled with the dressing member, providing the electrically conductive element comprising providing a conductive thread and providing an extended antenna, providing the extended antenna comprising embedding the extended antenna in the dressing member, and providing the electrically conductive element comprising configuring the electrically conductive element, via the conductive thread, to sense a plurality of parameters comprising pressure information and moisture information in the effective area; and
providing a primary RFID device coupling a primary severed antenna with the electrically conductive element, providing the primary RFID device comprising configuring the primary RFID device to transmit at least one output signal to the electromagnetically conductive element, to receive at least one return signal from the electromagnetically conductive element, and to provide an alert, via the primary severed antenna, if the at least one return signal has a strength corresponding to at least approximately a threshold amount of fluid present in the dressing member, providing the primary RFID device comprising configuring the primary RFID device to receive at least one return signal from the electromagnetically conductive element that is variable in relation to an ionic content of a wound discharge relative to an ionic content of water alone, providing the primary RFID device comprising configuring the primary RFID device to sense changes in dampness of the dressing member, and providing the primary RFID device comprising configuring the primary RFID device to measure and transmit, via the primary severed antenna, information relating to a plurality of parameters comprising the pressure information and the moisture information in the effective area,
wherein the fluid comprises the wound discharge,
wherein the strength of the at least one return signal is variable in relation to the ionic content of the wound discharge relative to the ionic content of the water alone, and
wherein providing the electromagnetically conductive element comprises providing the electromagnetically conductive element as embedded, interlaced, and interwoven in relation to the dressing member.

11. The method of claim 10, wherein providing the dressing member comprises providing at least one of a bandage and a compression bandage.

12. The method of claim 10, wherein providing the primary RFID device comprises further configuring the primary RFID device to measure and transmit, via the primary severed antenna, information relating to at least one parameter of a dressing application time, a calibration, and any other relevant parameter.

13. The method of claim 12, further comprising providing a secondary RFID device coupling a secondary severed antenna with at least one temperature sensor, providing the secondary RFID device comprising configuring the secondary RFID device to communicate, via the secondary severed antenna, with the primary RFID device and to receive and transmit, via the secondary severed antenna, the information relating to temperature information in the effective area.

14. The method of claim 13,
wherein providing the primary RFID device comprises providing a passive read-only RFID tag, providing the passive read-only RFID tag comprises configuring the passive read-only RFID tag to electromagnetically communicate with the electromagnetically conductive element,
wherein providing the secondary RFID device comprises providing a passive read-write RFID tag, providing the passive read-write RFID tag comprises configuring the passive read-write RFID tag to electromagnetically communicate with at least the passive read-only RFID tag,
wherein at least one of providing the primary RFID device and providing the secondary RFID device comprises respectively providing the primary RFID device and providing the secondary RFID device as sterilizable by gamma radiation and clean-in-place (CIP) sterilization, and
wherein at least one of providing the primary RFID device and providing the secondary RFID device comprises respectively providing the primary RFID device and providing the secondary RFID device as compliant with a Restriction of Hazardous Substances (RoHS) Directive.

15. The method of claim 13, wherein providing the primary RFID device and providing the secondary RFID device, comprises providing configuring the primary RFID device and configuring the secondary RFID device, together, to cooperate in a passive operation mode.

16. The method of claim 13, further comprising providing at least one temperature sensor for monitoring a wound temperature, wherein providing the primary RFID device, providing the secondary RFID device, and providing the at least one temperature sensor, comprise providing the primary RFID device, providing the secondary RFID device, and providing the at least one temperature sensor, together, to cooperate in an active operation mode.

17. The method of claim 16, wherein providing the at least one temperature sensor comprises providing at least one of a micro-thermocouple having an ending portion and a micro-thermistor, and wherein providing the at least one temperature sensor comprises providing the at least one temperature sensor as at least one of disposable, biocompatible, and sterilizable.

* * * * *